United States Patent [19]

O'Brien et al.

[11] Patent Number: 4,783,526

[45] Date of Patent: Nov. 8, 1988

[54] CHLORINATION OF CARBOHYDRATES AND OTHER ALCOHOLS

[75] Inventors: Eleanor A. O'Brien; Thomas O'Connor; Mathew R. J. Tuite, all of Dublin, Ireland; Leroy B. High, Cranbury, N.J.

[73] Assignee: McNeilab, Inc., Spring House, Pa.

[21] Appl. No.: 921,293

[22] Filed: Oct. 20, 1986

[30] Foreign Application Priority Data

Oct. 21, 1985 [GB] United Kingdom ............... 8525954

[51] Int. Cl.$^4$ .................... C07H 3/04; C07H 1/00; C07H 5/02
[52] U.S. Cl. ................... 536/18.5; 536/18.4; 536/122; 536/124; 536/125
[58] Field of Search ............. 536/18.4, 18.5, 124, 536/125, 122

[56] References Cited

U.S. PATENT DOCUMENTS

| | | | |
|---|---|---|---|
| 3,715,407 | 2/1973 | Relles | 556/144 |
| 4,343,934 | 8/1982 | Jenner et al. | 536/122 |
| 4,362,869 | 12/1982 | Jenner et al. | 536/122 |
| 4,612,373 | 9/1986 | Khan et al. | 536/122 |
| 4,692,514 | 9/1987 | Chang | 536/127 |

FOREIGN PATENT DOCUMENTS 45-19488 7/1970 Japan ................... 536/125

Primary Examiner—Ronald W. Griffin
Assistant Examiner—Nancy S. Carson
Attorney, Agent, or Firm—Steven P. Berman

[57] ABSTRACT

Chlorination of carbohydrates and alcohols utilizing a chlorinating reagent selected from triphenylphosphine oxide/thionyl chloride, thiphenylphosphine oxide/phosgene, triphenylphosphine sulfide/thionyl chloride and triphenylphosphine sulfide/phosgene.

6 Claims, No Drawings

CHLORINATION OF CARBOHYDRATES AND OTHER ALCOHOLS

BACKGROUND OF THE INVENTION

This invention relates to a process for the chlorination of carbohydrates and other alcohols. More particular, this invention relates to a process for the preparation of 1,6-dichloro-1,6-dideoxy-β-D-fructofuranosyl-4-chloro-4-deoxy-α-galactopyranoside. This compound is a potent sweetener, having a sweetness several hundred times that of sucrose. Its use as a sweetener and in sweetening compositions is disclosed in U.S. Pat. No. 4,435,440.

The preparation of 1,6-dichloro-1,6-dideoxy-β-D-fructofuranosyl-4-chloro-4-deoxy-α-galactopyranoside or as it is sometimes referred to in the literature, 4,1',6'-trichloro-4,1',6'-trideoxygalactosucrose (hereinafter referred to as "sucralose") involves the substitution of chlorine atoms in the sucrose molecule in one of the five secondary hydroxyl positions and in two of the three primary hydroxyl positions. This particular selection of positions usually means that any synthetic route must involve the preparation of an intermediate sucrose derivative having the required positions available for chlorination while other positions are blocked. In particular, the reactive 6-position must not be chlorinated, while the 4-position must be rendered available for chlorination.

One route proposed in the literature (Fairclough et al, Carbohydrate Research 40 (1975) 285-298) involves the formation of the 6,1',6'-tritrityl derivative of sucrose, peracetylation of the molecule and then detritylation with migration of the 4-acetyl radical to the 6-position, to give 2,3,6,3',4'-penta-O-acetylsucrose which has the correct hydroxy groups unprotected. Subsequent reaction with an excess of sulfuryl chloride as the chlorinating agent provides the 4,1',6'-trichlorogalactosucrose penta-acetate which in turn yields sucralose on elimination of the acetyl groups. The chlorination proceeds with inversion of configuration at the 4-position. The 1' and 6'-positions freely rotate, but the 4-position cannot and the glucose ring is thus inverted at the 4-position yielding a galactose derivative so that the product is a galactosucrose. The reaction sequence involving the simultaneous detritylation and acetyl shift contains, in all, a relatively high number of stages, and the initial tritylation reaction is undesirable from an economic point of view.

Another route is set forth in U.S. Pat. No. 4,380,476 and comprises the steps of; (a) reacting sucrose with an acylating reagent under conditions to provide a mixture of acylated sucrose derivatives containing a major proportion of 6-monoacylated material: (b) optionally separating the 6-monoacylated sucrose derivative from other acylated derivatives before step (c); (c) reacting the monoacylated sucrose derivative with a Vilsmeier type chlorinating reagent capable of chlorinating at positions 1', 4 and 6' of a sucrose 6-acylate; and (d) deacylating and separating (in either order) the sucralose material formed.

A further process for preparing sucralose is set forth in U.S. Pat. No. 4,362,869. This process converts sucrose through a number of steps into sucralose. This process describes the sequential steps of (1) tritylation of sucrose to block the three primary alcohol groups; (2) acetylation of the five secondary alcohol groups as acetates; (3) detritylation of the three primary alcohol groups to deblock them; (4) acetyl migration from the 4-position to the 6-position; (5) chlorinating the desired alcohol groups at positions 4, 1', 6'; and (6) deblocking the remaining five alcohol groups by deacetylation thereby yielding sucralose.

A number of chlorinating agents are disclosed in U.S. Pat. No. 4,362,869 including a chlorinating reagent consisting of triarylphosphine/carbon tetrachloride, N,N-dialkyl (chloromethan-iminium) chlorides and dichlorophosphoranes as well as other prior art chlorinating reagents.

While generally satisfactory in some cases, the chlorinating reagents disclosed in the above processes do present some problems. In some cases, the yields may be erratic due to decomposition and charring of the resultant products may be observed. Some of the above reactions are not efficient yielding incompletely chlorinated materials and when pyridine is involved as a solvent, the reactions are expensive due to the cost of the pyridine, the difficulty in recovering same and chlorinated by-products are formed which reduce recovery efficiencies.

It is an object of the present invention to provide a process for the chlorination of carbohydrates and other alcohols.

It is a further object of the present invention to provide an improved process for the preparation of sucralose.

It is a still further object of the present invention to provide an improved process for the preparation of sucralose wherein the chlorinating agent is efficient and eliminates the use of pyridine as a solvent.

These and other objects of the present invention will become apparent to one skilled in the art from the detailed description given hereinafter.

SUMMARY OF THE INVENTION

The foregoing objects and other features and advantages of the present invention are achieved by an improved process for the preparation of sucralose. This process comprises the steps of (1) tritylation of sucrose to block the three primary alcohol groups; (2) acetylation of the five secondary alcohol groups as acetates; (3) detritylation of the three primary alcohol groups to deblock them; (4) acetyl migration; (5) selective chlorination; and (6) deacetylation to deblock the remaining alcohol groups to yield sucralose.

Applicants have found that the desired results of the present invention can be achieved by utilizing a chlorinating reagent comprising triphenylphosphine oxide and thionyl chloride in a suitable solvent under specific reaction conditions.

German Pat. No. 1,192,205, issued Jan. 5, 1966, discloses a process for the preparation of triaryldihalides. This process involves the reaction of triaryloxides with inorganic acid halides in general and a triarylphosphine oxide, triarylarsine oxide or triarylstibine oxide with a chloride or bromide of carbonic acid or sulphurous acid in particular and thionyl chloride is mentioned in Example IV. It is alleged that triphenyl-phosphinedichlorides are produced and the overall reaction permits a simple recovery of triarylphosphines from triarylphosphine oxides by reducing the dichlorides with sodium.

U.S. Pat. No. 3,715,407 discloses a method for chlorinating ketones by reacting phosgene with phosphine oxides to obtain dichlorophosphorones which can then be used to convert ketonic acetyl groups to the corresponding chlorinated compounds. There is no suggestion of utilizing this reagent for the chlorination of carbohydrates or alcohols.

DETAILED DESCRIPTION OF THE INVENTION

As stated above, it has now been found that a chlorinating reagent comprising triphenylphosphine oxide and thionyl chloride performs extremely well.

The use of this chlorinating reagent offers some advantages over the chlorinating reagents of the prior art such as less impurities and side reactions, easy recoverability of the triphenylphosphine oxide, ease of chlorination and the like.

In the process for the preparation of sucralose, the use of the thionyl chloride/triphenylphosphine oxide reagent gives complete chlorination of all three free hydroxyl groups in 2,3,6,3′,4′-penta-O-acetyl sucrose (6-PAS), in high yield with none of the charring or extraneous biproduct formation usually associated with powerful chlorinating reagents acting on carbohydrates. The triphenylphosphine oxide is a catalyst and can be readily recovered for re-use.

The reaction solvent should be inert to chlorination and of sufficiently high boiling point to achieve complete chlorination in a reasonable time. Prolonged heating will cause some degradation. Solvents among others which are suitable are aromatic hydrocarbons such as toluene and xylene, higher boiling chlorinated hydrocarbons such as dichloroethane, and pyridine. Temperatures greater than 95° C. are generally necessary to achieve complete chlorination of the unreactive 1′ position, but the reaction does occur on long heating in the lower boiling solvents such as dichloroethane. Toluene is an eminently suitable solvent for the reaction having the correct reflux temperature and being a poor solvent for both triphenylphosphine oxide and 4,1′,6′-trichloro-4,1′,6′-trideoxygalactosucrose penta-acetate (TOSPA). The product and catalyst being readily isolated by crystallization.

The reaction can be easily monitored by thin layer chromatography and reaction times of 1–3 hr at reflux in toluene are suitable, preferably using about 2 equivalents of triphenylphosphine oxide and about 5 equivalents of thionyl chloride in toluene. Reflux is desirable to remove the gaseous biproducts, though the reaction has been carried out in xylene at 120° C. Temperatures above 120° C. are undesirable as thermal as opposed to chemical charring can occur.

Chlorination of 2,3,6,3′,4′-penta-O-acetyl sucrose also occurs using thionyl chloride and poly(diphenylphosphinoxido)styrene beads. The beads are readily filterable from the reaction mixture aiding recovery of the catalyst. The reaction is not as efficient as the solution reaction.

The use of the analogous triphenylphosphine sulfide/thionyl chloride combination has also been found satisfactory to effect complete chlorination of 6-PAS. However, since triphenylphosphine sulfide is consumed in the reaction, it cannot be directly recycled. It should also be noted that phosgene can be substituted for thionyl chloride.

As discussed above, the first step of the process involves the tritylation of sucrose to block the three primary alcohol groups. This can be accomplished by reacting sucrose with trityl chloride in a suitable solvent such as pyridine. It has also been noted that increased yields at lower costs can be achieved when the solvent is changed from pyridine to dimethylformamide using a tertiary amine acid scavenger such as N-methyl morpholine.

After completion of the reaction and the blocking of the three primary alcohols, the tritylated reaction product is subjected to in-situ peracetylation with acetic anhydride. If pyridine is used as a solvent, the reaction mixture after acetylation can be poured into ice water and the precipitated product filtered and dried. The procedure is repeated a number of times to remove any traces of pyridine and a crystallization yields 6,1′,6′-tri-O-trityl-sucrose penta-acetate. Other suitable methods of crystallization can also be utilized.

If dimethylformamide is used as the solvent during tritylation, then the N-methylmorpholine hydrochloride can be neutralized in-situ by the addition of sodium hydrogen carbonate and the solution is concentrated to remove N-methylmorpholine and a large portion of the dimethylformamide. Acetic anhydride and a suitable catalyst such as sodium acetate are then added to the residue. After reaction at 115° C. for 2 hours, the 6,1′,6′-tri-O-trityl-sucrose penta-acetate is crystallized from methanol. Alternatively, the tritylation can be carried out by adding the trityl chloride in toluene solution to the sucrose in dimethyl formamide/N-methylmorpholine. The water-soluble material is extracted with an aqueous wash and the tritrityl sucrose acetylated with acetic anhydride in toluene solution.

The detritylation step can be accomplished by dissolving the 6,1′,6′-tri-O-tritylsucrose penta-acetate in dichloromethane and acetic acid, cooling the solution to 0° C. and adding concentrated hydrochloric acid. After stirring for two hours, the solution is neutralized. After additional stirring and concentration, methanol is added resulting in the precipitation of triphenylmethanol. The solution is then concentrated and ether is added and 2,3,4,3′,4′-penta-O-acetylsucrose is crystallized out at room temperature.

Other methods of detritylating the 6,1′,6′-tri-O-tritylsucrose penta-acetate (TRISPA) can also be utilized. For example, hydrogen chloride can be reacted with the tritylated penta-acetate in toluene solution at about 0° C. with the 2,3,4,3′,4′-penta-O-acetylsucrose isolated by filtration and the trityl chloride recovered by concentration of the mother liquor. The detritylation can also be accomplished in a methylene chloride solution using hydrogen chloride as the catalyst in methanol with formic acid/methylene chloride/water, or using Lewis acid catalysts.

The acetyl migration can be achieved by treating the 2,3,4,3′,4′-penta-O-acetylsucrose in an inert solvent with a weak acid at an elevated temperature as in U.S. Pat. No. 4,362,869. The reaction is best carried out in a ketonic solvent boiling above 100° C. for example methyl isobutyl ketone, using about 1 to 6% solution of the carboxylic acid catalyst preferably acetic acid. The product is isolated by crystallization from the cooled solution by addition of a suitable diluent, such as heptane or other hydrocarbon solvents, filtration and drying.

Under certain conditions acetylation can take place leading to hexa or higher acetates which are very undesirable. To overcome this problem base catalysts were examined. The prior art reveals that dilute aqueous solutions of bases are suitable for carrying out acetyl migrations. Though the migration occurs from the 4 to the 6 positions of the glucose with 0.001N sodium hydroxide the yield is very low due to concurrent deacetylation. When 2–5% solutions of the very weak base pyridine or substituted pyridines, e.g. 2,4 and 2,6 lutidines or 2,4,6 tri-methyl pyridine (collidine) were used in water, reasonable yields of 2,3,6,3',4'-penta-O-acetyl sucrose were obtained. However, deacetylation and further migration to give 3,4,6,3',4'-penta-O-acetyl sucrose also occur.

An alternative method to achieve the acetyl migration is described in copending application Ser. No. 921,285 filed Oct. 20, 1986 and utilizes a weak base catalyst in a non-aqueous solvent. It has been found that weak bases such as aliphatic amines are suitable, but that pyridine and similar compounds are not, being too weakly basic. The base should be kinetically active but sterically hindered to inhibit deacetylation and to minimize side reactions.

Specific base catalysts which have been found useful include (in order of reactivity) 2 propylamine, tert-butylamine, n-butylamine, pyrolidine, piperidine, diethylamine, di-isopropyl-amine, morpholine, triethylamine and the like. The reaction temperature should be from 30° C. to 60° C. preferably about 50° C. If the temperature is raised above 60° C. then the risk of side reactions increases, whilst at temperatures below about 30° C. the reaction tends to be slow and, due to the insolubility of the 2,3,4,3',4'-penta-O-acetyl sucrose, does not go to completion. The acetyl migration reaction is in fact reversible, the equilibrium favoring the migrated product. 2,3,6,3',4'-penta-O-acetyl sucrose by about 4:1. However, if the product is only partially soluble it crystallizes out of the reaction mixture and drives the reaction to completion. Thus, the choice of solvent can materially affect the reaction efficiency.

The migration takes place in any inert solvent in which 2,3,4,3',4'-penta-O-acetyl sucrose is sparingly soluble, excluding alcohols or primary and secondary amines, where potential for a base catalyzed deacetylation reaction exists. The migration takes place in the following representative solvents: toluene, tetrahydrofuran, methylene chloride, ethyl acetate, acetone, acetonitrile, pyridine (with a stronger base catalyst like tert-butylamine). The best solvents are those in which the product being only partially soluble, crystallizes out early and drives the reaction to completion. Toluene, ethyl acetate and methyl isobutyl ketone are examples of this class. High amine concentration inhibits crystallization and for this reason the catalyst concentration should be in the range 2–6%. Under these conditions, good yields of 2,3,6,3',4'-penta-O-acetyl sucrose can be obtained.

The chlorination results in the formation of 4,1',6'-trichloro-4,1',6'-trideoxygalactosucrose penta-acetate. The deacetylation can be achieved with methanol and sodium methoxide to yield the desired sucralose.

Although the above description has been limited to a process for the preparation of sucralose in general and to specific chlorinating agents for use in that process, the invention should be viewed in broader aspects. The specific chlorinating agents disclosed in this application can be utilized to chlorinate compounds other than 2,3,6,3',4'-penta-O-acetyl sucrose (6-PAS). For example, the chlorinating agents of the present invention can be used to chlorinate other carbohydrates and alcohols such as mannitol, raffinose, ethylene glycol, 2-butanol, 1-adamantane methanol, 2-adamantanol, 1-adamantanol, sucrose, sucrose-6-acetate, sorbitol, substituted sorbitols and the like.

Specific embodiments of the present invention are illustrated by the following representative examples. It will be understood, however, that the invention is not confined to the specific limitations set forth in the individual examples but rather to the scope of the appended claims.

EXAMPLE I

Tritylation and Acetylation

Sucrose (50 g. 0.14 mol) is mixed with N-methylmorpholine (60 g. 0.59 mol) in dimethylformamide (100 mls) at 50° C. Tritylchloride (141.8 g of 97% purity, 0.49 mol) is added in three portions over 2.5 hours and heating continues for 3.5 hours. Sodium hydrogen carbonate (42.7 g, 0.5 mol) is added and heating at 50° C. continues for one hour. All solvents are removed under vacuum and the residue is dissolved in acetic anhydride (96.6 mls, 1.02 moles). Potassium acetate (15.6 g, 0.15 moles) is added and heating at 115° C. is undertaken for 3 hours. After cooling, methanol (400 mls) is added and after crystallization is complete a solid (183.2 g) is obtained which contains 6,1,6'-tri-O-tritylsucrose penta-acetate (TRISPA) (124.6 g, 68.6% yield).

EXAMPLE II

Tritylation and Acetylation

Sucrose (40 g, 0.11 mol) is mixed with N-methylmorpholine (50 g, 0.49 mol) in dimethylformamide (120 mls) at 50° C. Tritylchloride (95 g of 97% purity, 0.33 mol) dissolved in hot (60° C.) toluene (60 mls) is added in three portions over the same number of hours. Heating is continued for three further hours after which toluene (140 mls) is added. The mixture is extracted with 50 ml portions of brine at 60° C. (to prevent emulsions forming). On complete removal of the N-methylmorpholine hydrochloride and the dimethylformamide, the toluene/solution of 6,1',6'-tri-O-tritylsucrose is dried by azeotroping off the water. Acetylation with acetic anhydride (75 mls, 0.8 mol) and pyridine (5 mls) at 90° C. for 3 hours is followed by cooling and crystallization with methanol (420 mls) yielding a solid (112.7 g). The TRISPA content was 91.4% (103 g) implying a 68.9% yield.

EXAMPLE III

Detritylation

TRISPA (200 g) is dissolved in toluene (800 ml) and the solution is cooled to 0° C. Hydrogen chloride gas (17.1 g) is passed into the cooled stirred solution over 4.5 hours, after which the slurry of precipitated 4-PAS is stirred for 15 mins. The system is purged with nitrogen under vacuum for 1 hour to remove residual hydrogen chloride. The resultant mixture is filtered and washed with toluene (65 mls), granulated and reslurried in toluene containing 1% triethylamine (120 mls) for 10 mins. The mixture is again filtered, washed with toluene (65 ml) and dried, yielding 87 g (80%, corrected for assay) of 2,3,4,-3',4'-penta-O-acetylsucrose (4-PAS).

EXAMPLE IV

Detritylation

TRISPA (50 g) is dissolved in methylene chloride 150 mls. Methanol (15 ml. containing hydrogen chloride (0.5M), 0.2 equivalents) is added and the solution is stirred at room temperature for 4.5 hours. The hydrogen chloride is neutralized with tertiary butyl amine (1 ml). The methylene chloride and methanol is evaporated at room temperature under vacuum, leaving a solid. The solid is slurried in methanol (120 ml) for 30 minutes, water (6 ml) is added and stirring is continued for 10 minutes. The triphenyl methanol is filtered (28.4 g) and washed with a solution of water (2 ml) in methanol (48 ml). The filtrate is reduced to an oil under reduced pressure and ethyl acetate (100 ml) is added to azeotrope off any residual water. The oil was dried overnight at 40° C. under vacuum, yielding 26.4 g yield (58.2%) of product.

EXAMPLE V

Acetyl Migration

4-PAS (50 g) is dissolved in water (100 ml) with heating to 60° C. The hot solution is filtered and cooled to ambient. The pyridine base (collidine 2,4,6-trimethyl pyridine (2.5 ml)) is added and the resultant solution is stirred at ambient temperature for 2.5 hours. The solution is acidified with concentrated hydrochloric acid (2.5 ml) and extracted with methylene chloride ($2 \times 125$ ml). The combined extracts are concentrated to (50 ml) and heptane (50 ml) is added, the solution being stirred whilst crystallization takes place. The resultant precipitate is diluted by the addition of heptane ($2 \times 50$ ml) over 20 minutes and filtered. The crystals are washed with heptane (30 ml) and dried in vacuo at 45° C. for 16 hours, yielding 2,3,6,3',4'-penta-acetyl sucrose (6-PAS) (34 g, 58% correcting for assays).

EXAMPLE VI

Acetyl Migration

4-PAS (200 g) is mixed with ethylacetate (322 mls), heptane 28 mls) and tert butylamine (21 mls) at 50° C. for 5 hours. 6-PAS is observed to crystallize during the reaction but complete crystallization is obtained by the addition of heptane (124 mls) at the reaction temperature followed by cooling and stirring for 3 hours. After filtration and washing of the cake with a mixture of ethylacetate-heptane (100 mls) it is dried in a vacuum oven at 40° C. for 16 hours. A white solid (140.3 g) containing 85.4% 6-PAS (119.8 g) is obtained. Yield 85.4%.

EXAMPLE VII

Acetyl Migration

4-PAS (100 g) is heated at reflux in methylisobutyl ketone (500 ml) containing acetic acid (30 ml) for 3 hrs. The solution is cooled to ambient, heptane (500 ml) is added and the resultant 6-PAS is filtered, washed with heptane (100 ml) and dried. Yield 86 g. 85% corrected for assays.

EXAMPLE VIII

Chlorination

To a stirred slurry of 6-PAS (50 g) and triphenylphosphine-oxide (TPPO) (50.3 g) in toluene (150 ml), at ambient is added thionyl chloride (32.8 ml). The resulting solution is refluxed for 2.5 hours. Following cooling to 40° C., water (200 ml) is added and the mixture is stirred vigorously at 0° C. for 1 hour. Filtration and washing with toluene/water (1:2, 75 ml) affords crude 4,1',6'-trichloro-4,1',6'-trideoxy-galactosucrose pentaacetate (TOSPA) which is recrystallized from hot methanol (200 ml) by stirring at $-20°$ C. for 1 hour. Filtration affords recrystallized TOSPA (40 g. 75% yield correcting for assays).

EXAMPLE IX

Chlorination

To a slurry of 2,3,6,3',4'-penta-O-acetyl sucrose (6-PAS) (59 g, 90.4 mmol) and triphenylphosphine oxide (125.8 g, 454 mmol) in 1,2-dichloroethane was added thionyl chloride (32.8 ml, 452 mmol) at ambient and the mixture heated to reflux for 3 hours. Sodium bicarbonate (20 g) in 220 ml of water were added slowly and the biphasic mixture agitate for 0.5 hour. The organic layer was separated, evaporated to dryness under vacuum and methyl isobutyl ketone (150 ml) added. On cooling at 0° C. for 1 hour, triphenylphosphine oxide (ca. 98 g) separated and was isolated by filtration, washing the filter cake with methyl isobutyl ketone (50 ml). The mother liquor was evaporated to dryness under reduced pressure and the residue recrystallized from ethanol, giving 4,1',6'-trichloro-4,1',6'-trideoxy-2,3,6,3', 4'-penta-O-acetyl-galactosucrose (97.1 g), slightly contaminated with triphenylphosphine oxide.

EXAMPLE X

Chlorination

To a slurry of triphenylphosphine oxide (45 g. 0.162 mole) in toluene at 45° C. was charged phosgene (20 g, 0.202 mole). To the resulting mixture, agitate for 30 mins and subsequently degassed with nitrogen was added 6-PAS (20 g, 0.0362 mole), and the entire mixture refluxed (110°–114° C.) for 3 hours. On cooling to 20° C., 170 ml of water were added. On further holding at 0° C., for 1 hour, the mixture was filtered, affording 64.7 g of dry crude product, which on recrystallization from methanol, afforded 4,1',6'-tri-chloro-4,1',6'-trideoxy-2,3,6,3',4'-penta-O-acetyl-galactosucrose (8.9 g).

EXAMPLE XI

Chlorination

To a slurry of 6-PAS (50 g) and triphenylphosphine sulphide (53.3 g) in xylene (150 ml) was added thionyl chloride (32.8 ml) and the mixture was heated at 115° C. for 4.5 hr. Water (300 ml) was added and the biphasic mixture was vigorously stirred at 0° C. for 1 hr. The crude TOSPA was isolated by filtration and recrystallized from hot methanol (Yield 31.8 g. 66% corrected for assays).

EXAMPLE XII

De-Acetylation

TOSPA (50 g) is stirred at ambient with sodium methoxide (0.5 g) in methanol (125 ml) for 1.5 hours under vacuum. TOSPA dissolves within 10 mins and the solution is neutralized by stirring with Amberlite IRC 50 (H+) resin (7.5 g). The resin is removed by filtration and washed with methanol (25 ml), the filtrate and wash then being stirred with decolorizing charcoal (2 g) and celite (2 g) for 15 mins. The solution is clarified by filtration and concentrated to a froth in vacuo. The sucralose is crystallized from ethyl acetate (100 ml), filtered, washed with ethyl acetate (25 mls) and dried in vacuo at 40° C. for 12 hours. Yield 26 g, 92% correcting for assays.

EXAMPLE XIII

Chlorination of 2-Butanol

A mixture of 9.17 ml of 2-butanol (100 mmol), 18.37 g triphenylphosphine oxide and 11.98 ml of thionyl chloride (166 mmol) are reacted for 3 hours at 65° C. 150 ml of ether is then added to the cooled mixture and the temperature is reduced to 0° C. and then 20 ml of water are added. The precipitated triphenylphosphine oxide is filtered and the ether layer is separated. The resultant product is further washed with 20 ml of water and dried over magnesium sulfate. The ether is evaporated and the 2-chlorobutane distilled at 68° C. Yield 47%.

EXAMPLE XIV

Chlorination of 1-adamantane methanol 91.66 g of 1-adamantane methanol (10 mmol), 2.78 g triphenylphosphine oxide (100 mmol), 1.44 ml of thionyl chloride (20 mmol) and 5 ml of toluene are mixed at room temperature. The reaction mixture is refluxed at 85° C. for 1½ hours and then 1.44 ml of thionyl chloride are added and the reaction is followed on thin layer chromatography. The eluent system is heptane, methanol and acetone in a 10:1:4 ratio respectively. After 3 hours, 20 ml of water and 15 ml of toluene are added. The organic layer is separated and washed with 10 ml of water. The toluene is separated and evaporated to dryness and then washed with 50 ml of heptane which is evaporated leaving 1.78 g of an oil which is the desired product. Yield 96.2%.

EXAMPLE XV

Chlorination of 2-adamantanol 1.52 g of 2-adamantanol (10 mmol), 2.78 g triphenylphosphine oxide (10 mmol) and 1.44 ml of thionyl chloride (20 mmol) are heated at 80° C. for 2 hours. A further 1.44 ml of thionyl chloride is added and heating continues for 2 additional hours. The work-up procedure of Example XIII is followed and results in 1.48 g of a solid product. Yield 86%.

EXAMPLE XVI

Chlorination of 1-adamantanol 1.52 g of 1-adamantanol (10 mmol), 2.78 g triphenylphosphine oxide (10 mmol) and 1.44 ml of thionyl chloride (20 mmol) are reacted in 5 ml of toluene and followed on thin layer chromatography. The work-up procedure of Example XIII is followed and results in 1.48 g of a solid product. Yield 86%.

EXAMPLE XVII

Chlorination of 1,4:3,6-dianhydrosorbitol 1.46 g of 1,4:3,6-dianhydrosorbitol, 5.57 g of triphenylphosphine oxide, 2.88 ml of thionyl chloride and 10 ml of toluene are mixed and heated at 80° C. for 5 hours. An additional 1.44 ml of thionyl chloride are added and the reaction mixture is left overnight at room temperature. 20 ml of water are added and the organic layer is separated and washed with a further 10 ml of water. The toluene is removed under vacuum and the resulting material is taken up in heptane. This is filtered and the filtrate gives 0.77 g of product. Yield 42%.

What is claimed is:

1. In a process for the preparation of 1,6-dichloro-1,6-dideoxy-$\beta$-D-fructofuranosyl-4-chloro-4-deoxy-$\alpha$-galactopyranoside comprising the steps of:
   (a) reacting sucrose with a tritylating agent;
   (b) acetylating the tritylated reaction product with an acetylating agent to obtain 6,1',6'-tri-O-tritylsucrose penta-acetate;
   (c) detritylating the 6,1',6'-tri-O-tritylsucrose pentaacetate to obtain 2,3,4,3',4'-penta-O-acetylsucrose;
   (d) isomerizing the 2,3,4,3',4'-penta-O-acetylsucrose to obtain 2,3,6,3',4'-penta-O-acetylsucrose;
   (e) chlorinating 2,3,6,3',4'-penta-O-acetylsucrose with a chlorinating reagent to obtain 4,1',6'-trichloro-4,1',6'-trideoxygalactosucrose pentaacetate; and
   (f) deacetylating the chlorinating product; the improvement comprising effecting the chlorinating step utilizing a chlorinating reagent selected from the group consisting of triphenylphosphine oxide/thionyl chloride, triphenylphosphine oxide/phosgene, triphenylphosphine sulfide/thionyl chloride and triphenylphosphine sulfide/phosgene in the presence of an aromatic hydrocarbon solvent at a temperature up to about 120° C.

2. A process according to claim 1 wherein the chlorinating reagent is triphenylphosphine oxide/thionyl chloride.

3. A process according to claim 1 wherein the tritylating agent in step (a) is trityl chloride.

4. A process according to claim 1 wherein the acetylating agent in step (b) is acetic anhydride.

5. A process according to claim 1 wherein the aromatic hydrocarbon is selected from the group consisting of toluene and xylene.

6. A process according to claim 1 wherein the aromatic hydrocarbon is toluene.

* * * * *